United States Patent [19]

Shoesmith

[11] Plant 5,026

[45] Apr. 5, 1983

[54] CHRYSANTHEMUM NAMED QUAKER (G6-217-WS)

[75] Inventor: May Shoesmith, Woking, England

[73] Assignee: Pan American Plant Co., Parrish, Fla.

[21] Appl. No.: 312,945

[22] Filed: Oct. 19, 1981

[51] Int. Cl.[3] ..... A01H 5/00

[52] U.S. Cl. ..... Plt./74

[58] Field of Search ..... Plt./74-75

*Primary Examiner*—Robert E. Bagwill

*Attorney, Agent, or Firm*—Chas. W. Rummler

[57] ABSTRACT

A new white daisy-like chrysanthemum suitable for year round production in four-inch pots, generally with a seven week response, and distinguished by a profuse production of medium sized flowers having spoon-tipped ray florets. This plant is also well suited for garden culture and if planted as vegetative cuttings and pinched until flower initiation, the result will be a large mound of white by the time the plants flower.

3 Drawing Figures

BACKGROUND OF THE NEW PLANT

This white daisy-like chrysanthemum originated as a seedling of unknown parentage growing in a field of plants grown from miscellaneous seeds collected by me from random pollinated greenhouse chrysanthemums and planted in greenhouse at West Chicago, Ill., in the hope of finding new and interesting varieties. This plant was discovered by me in 1976 and, because of the form and color of its flowers, was propagated by cuttings at West Chicago, Ill. Several generations of successive propagation of this plant have shown that its novel characteristics hold true and appear to be firmly fixed. This variety is now being grown for the commercial market at Cortez, Fla., as well as at West Chicago, Ill.

DESCRIPTION OF THE DRAWINGS

This new chrysanthemum variety is illustrated by the accompanying drawings, of which sheet one is a full color photographic view showing a mound of garden plants in full bloom; sheet two is a machine copy of the top side of typical leaves of this new variety; and sheet three is a machine copy of the bottom or back side of the same leaves.

DESCRIPTION OF THE NEW PLANT

The following is a detailed description of my new chrysanthemum variety based upon observations of plants grown in greenhouse at West Chicago, Ill., and made in the Spring of 1981, the color designations being according to The R.H.S. Colour Chart published by The Royal Horticultural Society of London, England.

THE PLANT

Origin: Seedling.
Parentage: Unknown.
Classification:
- *Botanic.*—*Chrysanthemum morifolium.*
- *Commercial.*—Garden chrysanthemum suitable for four-inch pot culture.

Form: Perennial herbaceous bush.
Shape: Mound.
Height: Up to one meter.
Growth: Vigorous, strong and upright.
Branching character: Caespitose.
Foliage:

- *Quantity.*—Abundant.
- *Leaf size.*—Up to about 30 mm. wide and about 50 mm. long.
- *Leaf shape.*—Ovate with cleft margins.
- *Texture.*—Leathery.
- *Color.*—Upper side — 147A. Under side — 147B.
- *Leaflets.*—Many in number and of various sizes.
- *Petioles.*—Length — about 20 mm.
- *Venation.*—Pinnate.
- *Rachis.*—About 40 to 50 mm. long.

THE BUD

Form: Globular.
Size: The size varies in both diameter and depth.
Opening rate: Typical chrysanthemum.
Color of florets:
- *When phyllaries first divide.*—150D.
- *When petals begin to unfurl.*—150D.

Phyllaries:
- *Number.*—Approximately 16.
- *Shape.*—Lanceolate.
- *Color.*—138C.

Peduncle: Rigid and erect and of various lengths.
- *Surface aspect.*—Pubescent.
- *Color.*—138C.

THE FLOWER

Blooming habit: Intermittent with profuse blooming in the Fall.
Blooms:
- *Size.*—Medium. Diameter — about 55 to 80 mm. Depth — flat.

Borne: Cyme.
Form: A single (daisy) composite inflorescence borne on a receptacle surrounded by an involucre of bracts.
Shape:
- *When bloom first opens.*—Cup-shaped.
- *When bloom matures.*—Flat.

Petalage:
- *Ray florets.*—Approximately 34 in number.
- *Disc florets.*—Very many.
- *Arrangement.*—Imbricated.
- *Form.*—Spoon tipped with rounded apex and entire margins.

Texture: Soft.
Appearance: Satiny.
Color:

*Ray florets.*—155D on both front and reverse sides.

*Disc florets.*—Yellow.

Persistence: The florets hang on and dry.

Peduncle: Strong, upright and of various lengths.

*Color.*—138C.

Fragrance: Typical chrysanthemum.

Lasting quality:

*On plant.*—About three weeks.

*As cut flower.*—Not recommended.

REPRODUCTIVE ORGANS

Stamens.

*Arrangement.*—Syngenesious.

*Number.*—Many.

*Anthers.*—Size — insignificant. Color — yellow.

*Filaments.*—Yellow in color and of insignificant length.

*Pollen.*—Color — yellow.

Pistils:

*Number.*—One for each floret.

*Styles.*—Of insignificant length and color.

Stigmas: Of insignificant color.

This new chrysanthemum is particularly adaptable for year round production in small pots and produces a distinct white daisy-like flower with spoon-tipped ray florets. This chrysanthemum may also be grown in and is well suited for garden culture and if planted as vegetative cuttings and pinched until flower initiation, this variety will produce a large mound of white by the time it flowers.

I claim:

1. A new and distinct chrysanthemum variety, substantially as herein shown and described, distinguished by its profuse production of white daisy-like flowers having spoon-tipped ray florets, by its adaptability to year round production in small pots, and by its suitability to be grown as a garden chrysanthemum.

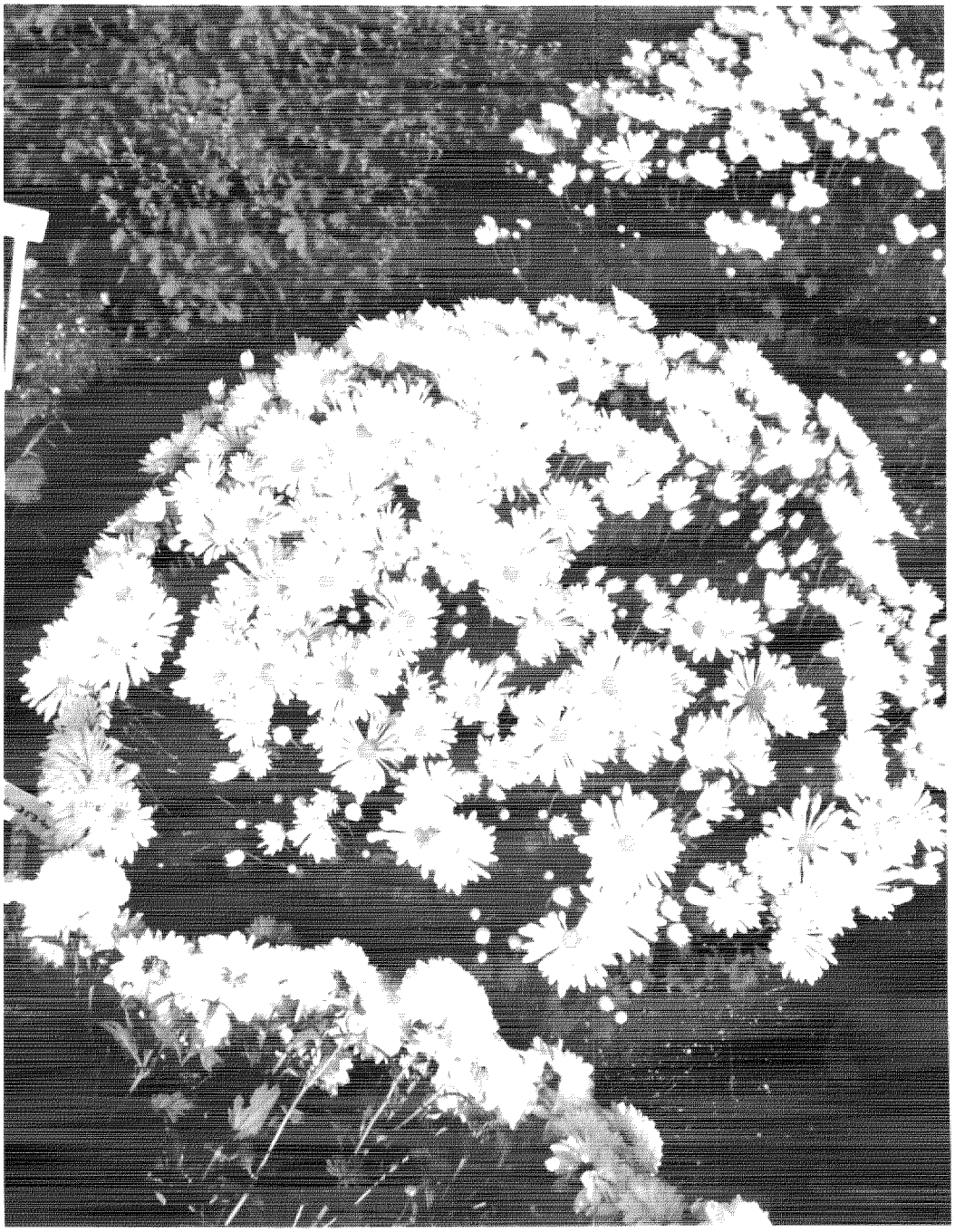

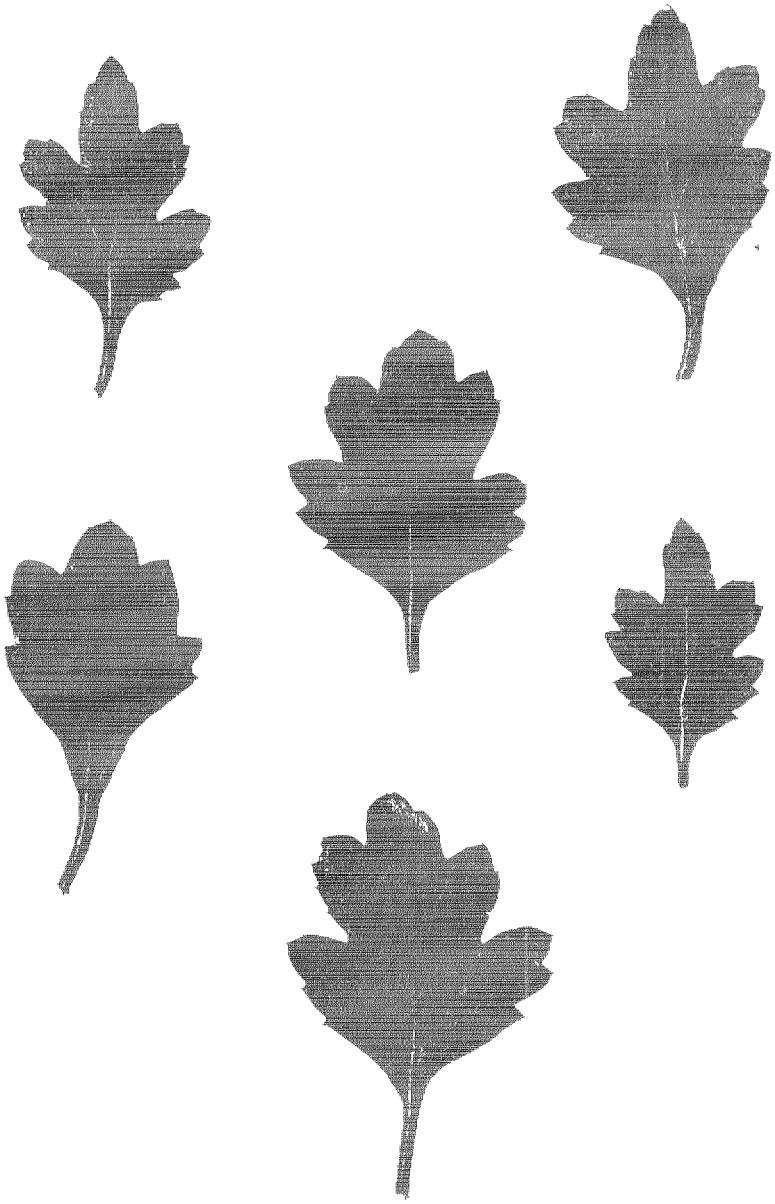

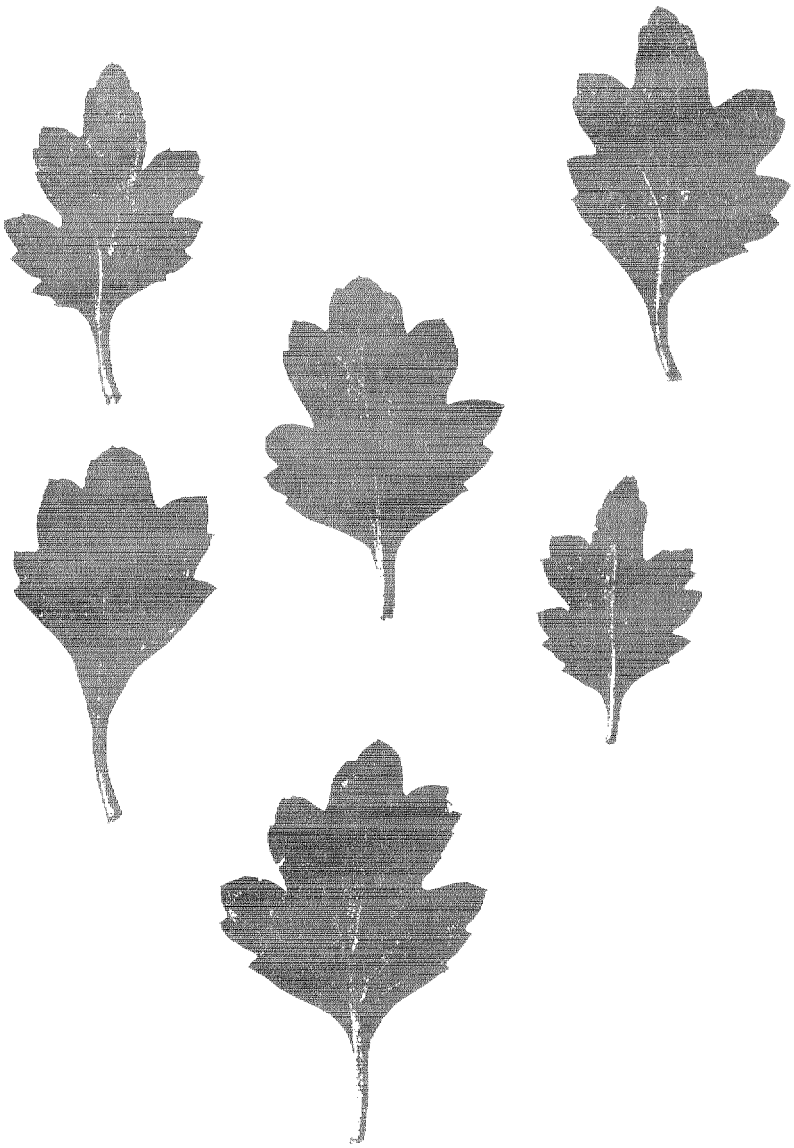

* * * * *